US008554365B2

(12) United States Patent
Thomas et al.

(10) Patent No.: US 8,554,365 B2
(45) Date of Patent: Oct. 8, 2013

(54) STORAGE DEVICES, SYSTEMS, AND METHODS FOR FACILITATING MEDICATION DISPENSING AND RESTOCKING (75) Inventors: Ryan Thomas, Wexford, PA (US); James Kolodziej, Aliquippa, PA (US); Pat Braun, Pittsburgh, PA (US); Jyotsna Rao, Pittsburgh, PA (US); Ben Tylenda, Venetia, PA (US); Shawn Greyshock, Tarentum, PA (US)

(73) Assignee: McKesson Automation Inc., Cranberry, PA (US)

( * ) Notice: Subject to any disclaimer, the term of this patent is extended or adjusted under 35 U.S.C. 154(b) by 183 days.

(21) Appl. No.: 13/076,762

(22) Filed: Mar. 31, 2011

(65) Prior Publication Data
US 2012/0253510 A1 Oct. 4, 2012

(51) Int. Cl.
G06F 17/00 (2006.01)
(52) U.S. Cl.
USPC ........... 700/242; 700/236; 700/237; 700/240; 700/241
(58) Field of Classification Search
USPC .......................... 700/236, 237, 240, 241, 242
See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |

(Continued)

OTHER PUBLICATIONS

Automated Systems [online] [retrieved Apr. 22, 2011]. Retrieved from the Internet: <URL: http://www.omnicell.com/Resources/Datasheets/Pharmacy-Drawer-Modules.pdf>. 4 pages.

(Continued)

Primary Examiner — Timothy Waggoner
(74) Attorney, Agent, or Firm — Alston & Bird LLP (57) ABSTRACT A storage device, method, and computer program product is provided that includes a number of drawer-level display devices. Each drawer-level display device may be associated with and disposed on a particular drawer. Each drawer-level display device may be configured to present a user with medication information for a selected medication stored in the associated drawer. Thus, a user can have direct access to information required for completing a dispensing or restocking operation at the accessed drawer and does not need to refer back to the cabinet-level display device for information. The drawer-level display devices may be main drawer-level display devices, located near a leading end of each drawer, and/or secondary drawer-level display devices located at the pockets defined by the drawer. Thus, the information needed to complete a dispensing or restocking operation that is in progress can be found at the drawer-level, where the user's attention is already focused.

25 Claims, 8 Drawing Sheets (56) References Cited

U.S. PATENT DOCUMENTS

| | | | |
|---|---|---|---|
| 5,661,978 | A | 9/1997 | Holmes et al. |
| D384,578 | S | 10/1997 | Wangu et al. |
| 5,713,485 | A | 2/1998 | Liff et al. |
| 5,716,114 | A | 2/1998 | Holmes et al. |
| 5,745,366 | A * | 4/1998 | Higham et al. ............... 700/242 |
| 5,761,877 | A | 6/1998 | Quandt |
| 5,797,515 | A | 8/1998 | Liff et al. |
| 5,805,456 | A | 9/1998 | Higham et al. |
| 5,842,976 | A | 12/1998 | Williamson |
| 5,878,885 | A | 3/1999 | Wangu et al. |
| 5,880,443 | A | 3/1999 | McDonald et al. |
| 5,883,806 | A | 3/1999 | Meador et al. |
| 5,893,697 | A | 4/1999 | Zini et al. |
| 5,905,653 | A | 5/1999 | Higham et al. |
| 5,912,818 | A | 6/1999 | McGrady et al. |
| 5,927,540 | A | 7/1999 | Godlewski |
| 5,940,306 | A | 8/1999 | Gardner et al. |
| 5,971,593 | A | 10/1999 | McGrady |
| 6,003,006 | A | 12/1999 | Colella et al. |
| 6,011,999 | A | 1/2000 | Holmes |
| 6,021,392 | A | 2/2000 | Lester et al. |
| 6,039,467 | A | 3/2000 | Holmes |
| 6,065,819 | A | 5/2000 | Holmes et al. |
| 6,068,156 | A | 5/2000 | Liff et al. |
| 6,109,774 | A | 8/2000 | Holmes et al. |
| 6,112,502 | A | 9/2000 | Frederick et al. |
| 6,116,461 | A | 9/2000 | Broadfield et al. |
| 6,151,536 | A * | 11/2000 | Arnold et al. ............... 700/237 |
| 6,170,230 | B1 | 1/2001 | Chudy et al. |
| 6,176,392 | B1 | 1/2001 | William et al. |
| 6,189,727 | B1 | 2/2001 | Shoenfeld |
| 6,223,934 | B1 | 5/2001 | Shoenfeld |
| 6,256,967 | B1 | 7/2001 | Hebron et al. |
| 6,283,322 | B1 | 9/2001 | Liff et al. |
| 6,289,656 | B1 | 9/2001 | Wangu et al. |
| 6,338,007 | B1 | 1/2002 | Broadfield et al. |
| 6,339,732 | B1 | 1/2002 | Phoon et al. |
| 6,361,263 | B1 | 3/2002 | Dewey et al. |
| 6,370,841 | B1 | 4/2002 | Chudy et al. |
| 6,449,927 | B2 | 9/2002 | Hebron et al. |
| 6,471,089 | B2 | 10/2002 | Liff et al. |
| 6,497,342 | B2 | 12/2002 | Zhang et al. |
| 6,499,270 | B2 | 12/2002 | Peroni et al. |
| 6,532,399 | B2 | 3/2003 | Mase |
| 6,564,121 | B1 | 5/2003 | Wallace et al. |
| 6,581,798 | B2 | 6/2003 | Liff et al. |
| 6,609,047 | B1 | 8/2003 | Lipps |
| 6,611,733 | B1 | 8/2003 | De La Huerga |
| 6,625,952 | B1 | 9/2003 | Chudy et al. |
| 6,640,159 | B2 | 10/2003 | Holmes et al. |
| 6,650,964 | B2 | 11/2003 | Spano, Jr. et al. |
| 6,671,579 | B2 | 12/2003 | Spano, Jr. et al. |
| 6,681,149 | B2 | 1/2004 | William et al. |
| 6,742,671 | B2 | 6/2004 | Hebron et al. |
| 6,755,931 | B2 | 6/2004 | Vollm et al. |
| 6,760,643 | B2 | 7/2004 | Lipps |
| 6,776,304 | B2 | 8/2004 | Liff et al. |
| 6,785,589 | B2 | 8/2004 | Eggenberger et al. |
| 6,790,198 | B1 | 9/2004 | White et al. |
| 6,814,254 | B2 | 11/2004 | Liff et al. |
| 6,814,255 | B2 | 11/2004 | Liff et al. |
| 6,847,861 | B2 | 1/2005 | Lunak et al. |
| 6,874,684 | B1 | 4/2005 | Denenberg et al. |
| 6,892,780 | B2 | 5/2005 | Vollm et al. |
| 6,895,304 | B2 | 5/2005 | Spano, Jr. et al. |
| 6,975,922 | B2 | 12/2005 | Duncan et al. |
| 6,985,797 | B2 | 1/2006 | Spano, Jr. et al. |
| 6,996,455 | B2 | 2/2006 | Eggenberger et al. |
| 7,010,389 | B2 | 3/2006 | Lunak et al. |
| 7,014,063 | B2 * | 3/2006 | Shows et al. ............... 221/211 |
| 7,016,766 | B2 | 3/2006 | William et al. |
| 7,040,504 | B2 | 5/2006 | Broadfield et al. |
| 7,052,097 | B2 | 5/2006 | Meek, Jr. et al. |
| 7,072,737 | B2 | 7/2006 | Lunak et al. |
| 7,072,855 | B1 | 7/2006 | Godlewski et al. |
| 7,077,286 | B2 | 7/2006 | Shows et al. |
| 7,085,621 | B2 * | 8/2006 | Spano et al. ............... 700/236 |
| 7,092,796 | B2 | 8/2006 | Vanderveen |
| 7,093,755 | B2 | 8/2006 | Jordan et al. |
| 7,100,792 | B2 | 9/2006 | Hunter et al. |
| 7,103,419 | B2 | 9/2006 | Engleson et al. |
| 7,111,780 | B2 | 9/2006 | Broussard et al. |
| 7,139,639 | B2 | 11/2006 | Broussard et al. |
| 7,150,724 | B2 | 12/2006 | Morris et al. |
| 7,171,277 | B2 | 1/2007 | Engleson et al. |
| 7,203,571 | B2 * | 4/2007 | Kirsch et al. ............... 700/236 |
| 7,218,231 | B2 | 5/2007 | Higham |
| 7,228,198 | B2 | 6/2007 | Vollm et al. |
| 7,249,688 | B2 | 7/2007 | Hunter et al. |
| 7,348,884 | B2 | 3/2008 | Higham |
| 7,417,729 | B2 | 8/2008 | Greenwald |
| 7,419,133 | B2 | 9/2008 | Clarke et al. |
| 7,426,425 | B2 | 9/2008 | Meek, Jr. et al. |
| 7,463,947 | B1 * | 12/2008 | Frederick et al. ............... 700/236 |
| 7,515,988 | B1 | 4/2009 | Frederick et al. |
| 7,554,449 | B2 | 6/2009 | Higham |
| 7,571,024 | B2 | 8/2009 | Duncan et al. |
| 7,588,167 | B2 | 9/2009 | Hunter et al. |
| 7,873,435 | B2 * | 1/2011 | Yuyama et al. ............... 700/237 |
| 8,280,550 | B2 * | 10/2012 | Levy et al. ............... 700/241 |

OTHER PUBLICATIONS

Automated Medication Solutions [online] [retrieved Apr. 22, 2011]. Retrieved from the Internet: <URL: http://www.omnicell.com/Resources/Datasheets/Automated-Medication-Dispensing-Systems.pdf>. 4pages.

Office Action for Canadian Application No. 2,772,891; dated May 13, 2013.

* cited by examiner

Dispense | Return | Med Mgt | Discrepancy | Admin

Select a Patient for Medication Dispense

Profile Dispense

Admit

Patient Info

Sort

Logout

Patients sorted by: Patient Name

Patient One, PAT001
SCRIPT0000000001    Admit Date: MM/DD/YYYY HH:MM    Allergies!
Unit: Outpatient    Room: 200                       Bed: 1

Patient Two, PAT002
SCRIPT0000000002    Admit Date: MM/DD/YYYY HH:MM
Unit: Outpatient    Room: 200                       Bed: 2

Patient Three, PAT003
SCRIPT0000000003    Admit Date: MM/DD/YYYY HH:MM
Unit: Outpatient    Room: 201                       Bed: 1

Patient Four, PAT004
SCRIPT0000000004    Admit Date: MM/DD/YYYY HH:MM
Unit: Outpatient    Room: 201                       Bed: 2

Patient Five, PAT005
SCRIPT0000000005    Admit Date: MM/DD/YYYY HH:MM
Unit: Outpatient    Room: 202                       Bed: 1

Patient Six, PAT006
SCRIPT0000000006    Admit Date: MM/DD/YYYY HH:MM
Unit: Outpatient    Room: 202                       Bed: 2

Patient Seven, PAT007
SCRIPT0000000007    Admit Date: MM/DD/YYYY HH:MM
Unit: Outpatient    Room: 203                       Bed: 1

Virtual 7.1 | AS | Receiving Orders | Discrepancies: 0

STORAGE DEVICES, SYSTEMS, AND METHODS FOR FACILITATING MEDICATION DISPENSING AND RESTOCKING

BACKGROUND

Automated dispensing cabinets (ADCs) are commonly used in healthcare facilities, such as hospitals, to provide healthcare professionals, such as nurses, with automated access to medication without requiring the pharmacy to fill patient-specific cassettes of unit-dose medications, which would then have to be delivered to the particular nursing unit and stored in non-automated medication cabinets or carts. In contrast, ADCs are computerized drug storage devices that allow nurses to automatically dispense medications to fill prescriptions near point of care, while at the same time tracking and controlling drug distribution.

Although ADCs have provided nurses with quicker and easier access to a patient's medications, the nurse is still required to spend a certain amount of time interacting with the ADC to dispense and restock medication. The more time and effort expended dispensing the medication, the less time the nurse has to directly interact with the patients to provide patient care. Considering the increasing numbers of patients who are admitted to healthcare facilities each year and the budgetary constraints on hiring additional healthcare professionals to care for these patients, every minute of a nurse's shift becomes even more valuable.

Furthermore, because the nurses are dispensing medication from an ADC storing a number of different medications, the potential for dispensing the wrong medication or the wrong dose of medication exists, especially in pockets that do not have a locked lid. This potential increases as nurses attempt to retrieve medication more quickly to enable them to return to their patients' bedsides.

Accordingly, there is a need in the art for an improved system and method for dispensing medication that allows healthcare professionals to dispense medication for the patients under their care in a more rapid, efficient, and accurate manner.

BRIEF SUMMARY OF THE INVENTION

Storage devices, systems, methods, and computer program products are therefore provided for dispensing medication. Embodiments of the storage devices, systems, methods, and computer program products allow users to more efficiently and effectively access medication stored in an automated storage device for filling patient prescriptions or restocking the storage devices, for example.

In one exemplary embodiment, a storage device for dispensing medication is provided that comprises at least one drawer and a plurality of drawer-level display devices. Each drawer may define a plurality of pockets, and each pocket may be configured to store at least one medication. Each of the drawer-level display devices may be associated with and disposed on a particular drawer and may be configured to present a user with medication information for a selected medication stored in the associated drawer. The medication information may include at least one of a name of the selected medication, a dosage of the selected medication, a quantity of the selected medication to be dispensed or restocked, or an inventory of the selected medication stored in an identified pocket. In some cases, the at least one drawer may be slideably received within the storage device.

In some embodiments, at least some of the drawer-level display devices may be main drawer-level display devices. In other embodiments, the plurality of drawer-level display devices may comprise, for each associated drawer, a main drawer-level display device disposed on the associated drawer and a plurality of secondary drawer-level display devices, where each secondary drawer-level display device is associated with and disposed proximate at least one of the pockets defined by the associated drawer. The main drawer-level display device may be configured to present a user with a name of the selected medication to be dispensed or restocked and an inventory of the selected medication stored in an identified pocket defined by the associated drawer. The secondary drawer-level display devices may each be configured to present to a user a quantity of the selected medication to be dispensed from or restocked to the associated pocket.

In some cases, the storage device may further include a plurality of drawer-level user input devices. Each drawer-level user input device may be associated with and disposed on a particular drawer, and each drawer-level user input device may be configured to receive input from a user regarding an inventory of the selected medication stored in an identified pocket defined by the associated drawer. The drawer-level user input device may be configured to receive input from a user selecting a workflow function. In addition, the storage device may further comprise a sensor configured to detect pocket access by a user during a medication dispensing or restocking operation.

In some embodiments, at least some of the drawer-level display devices may be secondary drawer-level display devices that are each associated with and disposed proximate at least one of the pockets defined by the associated drawer. Each secondary drawer-level display device may be configured to sequentially identify a single pocket defined by the associated drawer from which the selected medication is to be dispensed or to which the selected medication is to be restocked. Alternatively, at least some of the drawer-level display devices may be secondary drawer-level display devices that are each associated with and disposed proximate at least one of the pockets defined by the associated drawer, where the secondary drawer-level display devices are collectively configured to identify substantially simultaneously more than one pocket defined by the associated drawer from which the selected medication is to be dispensed or to which the selected medication is to be restocked.

In some cases, the storage device may further comprise a cabinet-level display device associated with the one or more drawers of the storage device and configured to present medication information related to any of the associated drawers. The storage device may further comprise a cabinet-level user input device associated with the one or more drawers of the storage device and configured to receive input from a user related to any of the associated drawers.

In other embodiments, a system for dispensing medication from a storage device is provided, where the storage device comprises a plurality of drawers. The system may include a processor configured to access medication information and a plurality of secondary drawer-level display devices in communication with the processor. Each secondary drawer-level display device may be associated with at least one of a plurality of pockets defined by a particular drawer, and each secondary drawer-level display device may be configured to identify at least one of the associated pockets from which a selected medication is to be dispensed and to present to a user a quantity of the selected medication to be dispensed from the identified pocket. In some cases, each secondary drawer-level display device may be configured to identify at least one of the associated pockets to which the selected medication is to be restocked.

Each secondary drawer-level display device may only be accessible to the user when the associated drawer is accessed by the user. In addition, the system may comprise a plurality of main drawer-level display devices in communication with the processor, where each main drawer-level display device is associated with one of the drawers of the storage device. Each main drawer-level display device may be configured to present to the user a name of the selected medication that is to be dispensed from or restocked to the associated drawer. In some cases, each main drawer-level display device may be disposed proximate a leading edge of the respective associated drawer and may be accessible to the user when the associated drawer is accessed by the user.

The system may further comprise a plurality of drawer-level user input devices in communication with the processor, and each drawer-level user input device may be associated with a particular drawer and may be configured to receive input from the user regarding an inventory of the selected medication stored in the identified pocket of the associated drawer. Each drawer-level user input device may be configured to receive input from the user regarding a workflow function.

In some cases, the system may further comprise a sensor in communication with the processor, wherein the sensor is configured to detect pocket access by the user during a medication dispensing or restocking operation. The processor may also be configured to present medication information regarding an additional selected medication to be dispensed or restocked based on feedback received from the sensor. In addition, the system may further include a cabinet-level display device in communication with the processor and configured to present to the user at least one item of information from the accessed medication information.

In still other embodiments, a method and a computer program product for dispensing medications are provided. Medication information relating to a first selected medication may be presented to a user via a cabinet-level display device associated with a storage device comprising at least one drawer. Furthermore, the user may be provided with access to a first identified drawer in which the first selected medication is stored, and a location of the first selected medication and a quantity of the first selected medication to dispense may be identified via at least one of a plurality of drawer-level display devices associated with and disposed on the first identified drawer. In some cases, identifying the location and the quantity of the first selected medication may comprise identifying a location of the first selected medication and a quantity of the first selected medication to restock via at least one of the plurality of drawer-level display devices.

In some cases, the storage device may further comprise a plurality of drawer-level user input devices, wherein at least one of the drawer-level user input devices is associated with a particular drawer and is disposed on the associated drawer. User input may be received via a drawer-level user input device associated with the first identified drawer. In addition, the user may be provided with access to a second identified drawer in which a second selected medication is stored based on the user input received. Furthermore, the user's access of a particular pocket defined by the first identified drawer and in which the first selected medication is stored may be sensed, and the user may be automatically provided with access to a second identified drawer in which a second selected medication is stored based on the access sensed.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Embodiments of the present inventions now will be described more fully hereinafter with reference to the accompanying drawings, in which some, but not all embodiments of the inventions are shown. Indeed, embodiments of these inventions may be embodied in many different forms and should not be construed as limited to the embodiments set forth herein; rather, these embodiments are provided so that this disclosure will satisfy applicable legal requirements. Like reference numerals refer to like elements throughout.

The storage devices, systems, and methods of embodiments of the present invention may be used by healthcare facilities, such as hospitals, physicians' offices, healthcare clinics, and any other facility that manages and/or dispenses drugs for patient use. The storage devices, systems, and methods described herein provide a more streamlined and efficient way for healthcare professionals to interface with an automated storage device, such as an automated dispensing cabinet (ADC), to dispense medications. Although nurses are often tasked with accessing medication stored in an automated storage device, and the example of a nurse is used in the description that follows, it is understood that the described embodiments apply to any user who is interfacing with the automated storage device, including physicians, pharmacists, nurses, laboratory personnel, and others. Furthermore, although the example of a user interfacing with an automated storage device to dispense medication is predominantly described below, one skilled in the art in light of this disclosure would recognize that the embodiments are also applicable to users interfacing with the automated storage device for the purpose of restocking medication, taking inventory, and performing other tasks that may require access to the medication stored in the automated storage device. Thus, for example, medication information such as the name of the selected mediation, the dosage, the quantity, etc. as described below may be provided for a selected medication to be restocked to a particular drawer and/or pocket. In other words, in addition to dispensing operations, embodiments of the storage devices, systems, methods, and computer program products described below may be equally applicable for restocking operations. In addition, the term "automated storage devices" is intended to include any type of automated storage device, including automated dispensing cabinets (ADCs), unit-based cabinets (UBCs), automated dispensing devices (ADDs), automated distribution cabinets, and automated dispensing machines (ADMs), among others.

Figure 1:
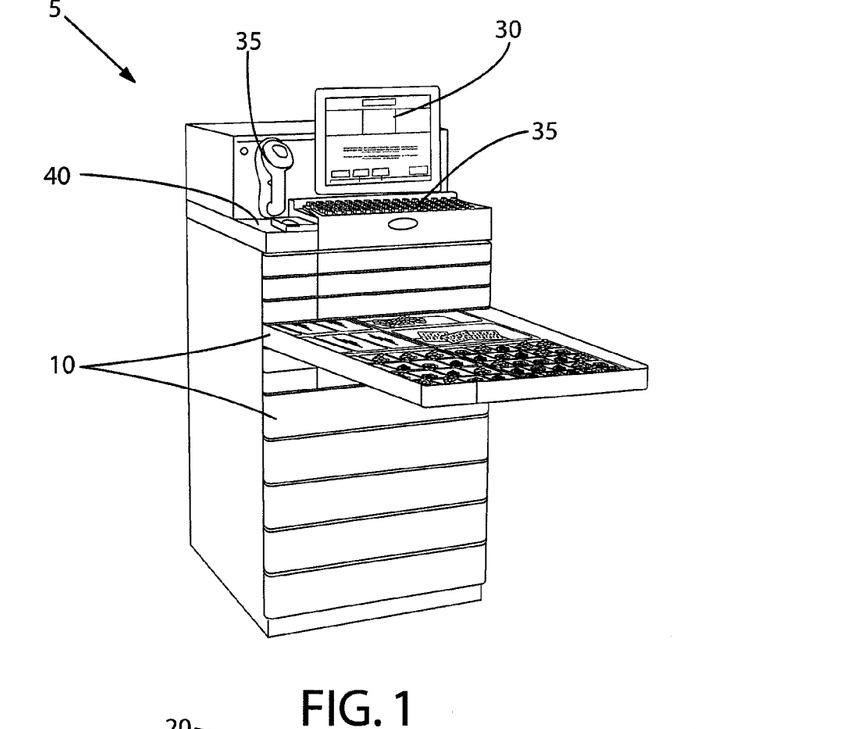
FIG. 1 illustrates an automated storage device in accordance with one exemplary embodiment.
Figure 1A:
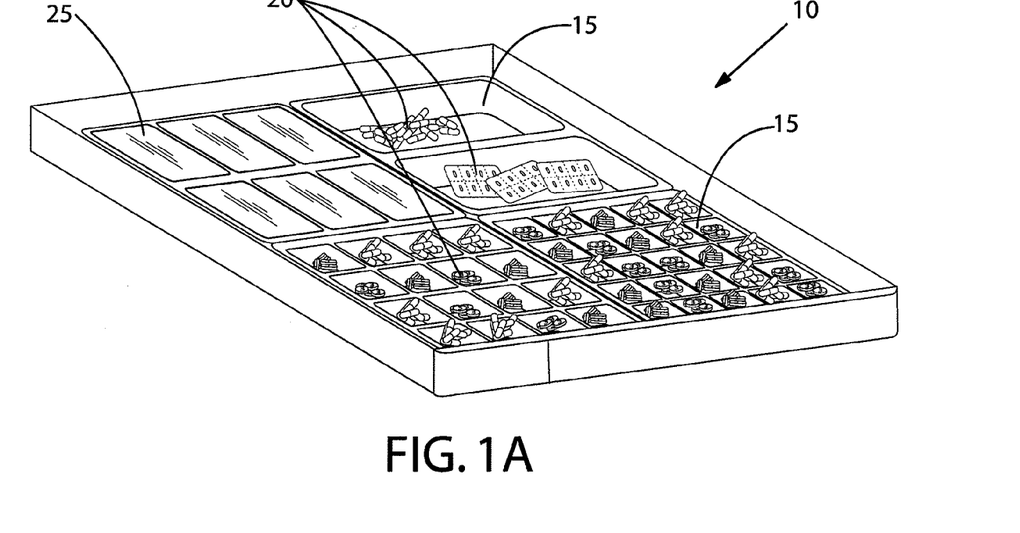
FIG. 1A illustrates a drawer of the storage device of FIG. 1 in accordance with one exemplary embodiment of the present invention.

Turning now to FIGS. 1 and 1A, an automated storage device 5 is shown. The storage device 5 may be configured to store a number of different types and quantities of medication. In this regard, the storage device 5 may include one or more drawers 10. The term "drawer" as used herein may refer to a structural division of space used for storing items. For example, the drawer 10 may be slideably received within the storage device 5, as depicted, or the drawer may be fixed within the storage device (such as, e.g., a shelf or the like).

Different types of storage devices 5 may include different sizes and styles of drawers 10, depending on the types of medications to be stored in the drawers, the quantities required (which may be dictated by the size of the facility), and user preferences. For example, as shown in FIG. 1, some drawers 10 may be deep, whereas others may be shallower. In addition, access to the drawers 10 may be restricted to certain authorized users and may further be accessible only when medication stored in the particular drawer is to be dispensed, as described in greater detail below. Accordingly, each drawer 10 may be in a locked state until an authorized user interfaces with the storage device 5 to dispense a particular medication stored within a particular drawer, at which point the storage device may unlock and/or open the drawer containing the selected medication to allow the user's access. In some cases, the storage device 5 may unlock all of its drawers 10 upon determining that a user is authorized to access the storage device, regardless of the location of the particular medication requested.

In this regard, as shown in FIG. 1A, each drawer 10 may define a plurality of pockets 15 that are each configured to store at least one medication 20 or type of medication. Thus, depending on the size, form (e.g., liquid, pill, capsule, etc.), packaging (e.g., cartridge strip, bottle, etc.), and/or special requirements for the medication (e.g., restricted access, such as a narcotic; medication requiring refrigeration; etc.), the configuration of the pocket 15 (e.g., size and shape) may also be different from one drawer 10 to the next or within the same drawer. For example, in the depicted embodiment of FIG. 1A, the pockets 15 defined by the open drawer 10 include four sizes of pockets to accommodate different types of medication. Furthermore, some pockets 15 may include lids 25 to keep the contents of the pocket in place. The lids 25 may be clear, to allow the user to view the contents of the pocket 15 with the lid closed, and others may be opaque, obscuring the view of the contents. In still other cases, the lids 25 may be locked (not shown) until access by an authorized user to the contents of the locked lid is granted, at which time the lid may be unlocked and/or opened to allow retrieval of the medication 20 stored therein.

In some embodiments, the storage device 5 further includes a cabinet-level display device 30, and a cabinet-level user input device 35. The cabinet-level display device 30 may be a monitor, as depicted, and may be configured to present various items of medication information for the user to view, as described below. The cabinet-level display device 30 may be associated with one or more of the drawers 10 of the storage device 5. In other words, the cabinet-level display device 30 may be configured to present information to the user regarding medication stored in multiple drawers 10 of the storage device 5 (e.g., on a cabinet level). In the depicted embodiment, for example, the cabinet-level display device 30 is associated with all of the drawers 10. Accordingly, the user may be able to view medication information related to any of the associated drawers 10 (e.g., regarding the contents of any of the drawers) via the cabinet-level display device 30. For example, the user may be able to view a list of patients under the user's care; view patient details (e.g., patient's name, date of birth, medical condition, allergies, date of admittance, date of expected discharge, etc.); view a list of prescribed medications for a particular patient; view medication details (such as potential interactions, medication properties, and dosage information); and/or view prescription details (such as the name of a prescribed medication, required dosage, quantity to be dispensed, location of the medication in the storage device (drawer and pocket), etc.).

Furthermore, in some cases, the cabinet-level display device 30 may be configured to present information to the user regarding medication stored in more than one storage device 5. For example, multiple storage devices 5 having the same or different storage capacity and/or configuration (such as towers, cabinets, and refrigerators) may be located in a room, floor, or hallway of the healthcare facility in close proximity to each other. In this case, the cabinet-level display device 30 may be centrally located and may be used by users desiring to access any one or more of the associated storage devices 5.

Similarly, the cabinet-level user input device 35 may be associated with one or more drawers 10 of the storage device 5 and may be configured to receive input from the user related to any of the associated drawers 10 (e.g., on a cabinet level). For example, the cabinet-level user input device 35 may be configured to receive user input regarding a particular dispensing operation (e.g., identification credentials authorizing the user to access the storage device 5 or a particular drawer 10 of the storage device; a selection of a patient for whom medication is to be dispensed; a request for information regarding a particular medication 20 stored in one of the associated drawers; a selection of a particular medication to be viewed or dispensed; etc.). As another example, the cabinet-level user input device 35 may be configured to receive user input regarding an inventory of a particular associated drawer 10 or multiple drawers. Furthermore, in some cases, the storage device 5 may be configured to communicate with other storage devices in other parts of the healthcare facility, such that the user may be able to enter input requesting information regarding the contents of the other storage devices (e.g., other storage devices associated with the cabinet-level display device 30 and located in the vicinity of each other, as noted above).

In some cases, more than one cabinet-level user input device 35 may be provided. For example, in the depicted embodiment, the storage device 5 includes both a keyboard and a barcode reader. The barcode reader may be configured to scan barcodes off medication packaging, and/or the barcode reader may be configured read a user's identification credentials (e.g., badge, bracelet, key, etc.) to ascertain whether the user has access to a particular storage device and/or access to a particular medication, as well as to track and trend access to the storage device, such as for taking inventory and generating reports regarding users. Other examples of cabinet-level user input devices may include a mouse and a touch screen keypad, among others. Furthermore, in some cases, the cabinet-level display device 30 is both a display device and a user input device, such as when the monitor is a touch screen that is configured to receive input via a user's touch selections of options that are presented on the screen.

Figure 2:
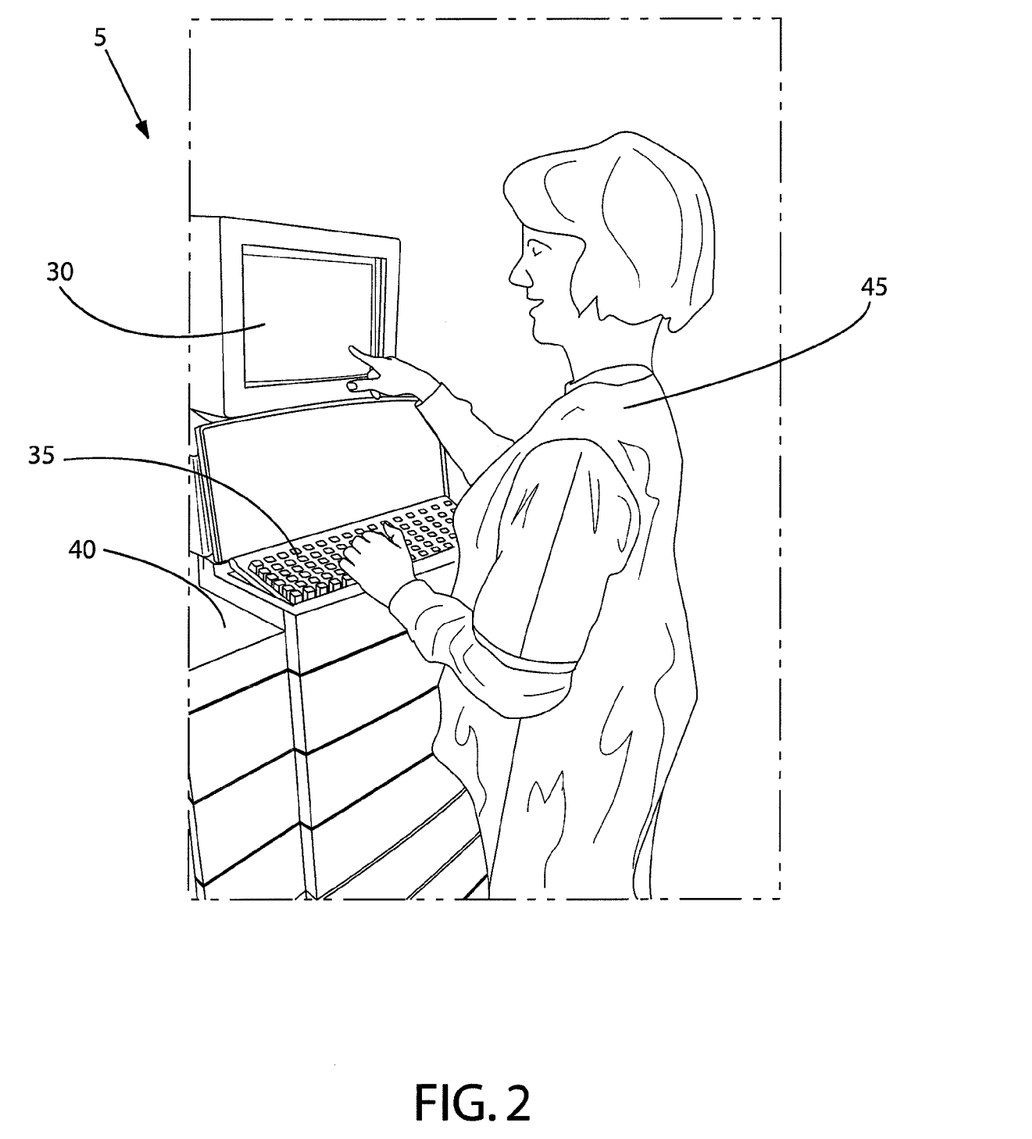
FIG. 2 illustrates a user accessing a cabinet-level display device in accordance with one exemplary embodiment of the present invention.

The cabinet-level display device 30 and the cabinet-level user input device(s) 35 may be disposed in a central location that is accessible to the user even when the drawers 10 are closed, such as on an upper surface 40 of the storage device 5. As shown in FIG. 2, the location of the cabinet-level display device 30 and the cabinet-level user input device 35 on a top surface 40 of the storage device 5 allows the user 45, such as the nurse, to have comfortable access to the cabinet-level display device and the cabinet-level user input device when standing in front of the storage device, as shown, or an associated storage device nearby. In this way, the nurse 45 may be able to view and manipulate various types of medication information upon first approaching the storage device 5, in the standing position (e.g., before accessing any of the drawers 10 to dispense medication).

Figure 3:
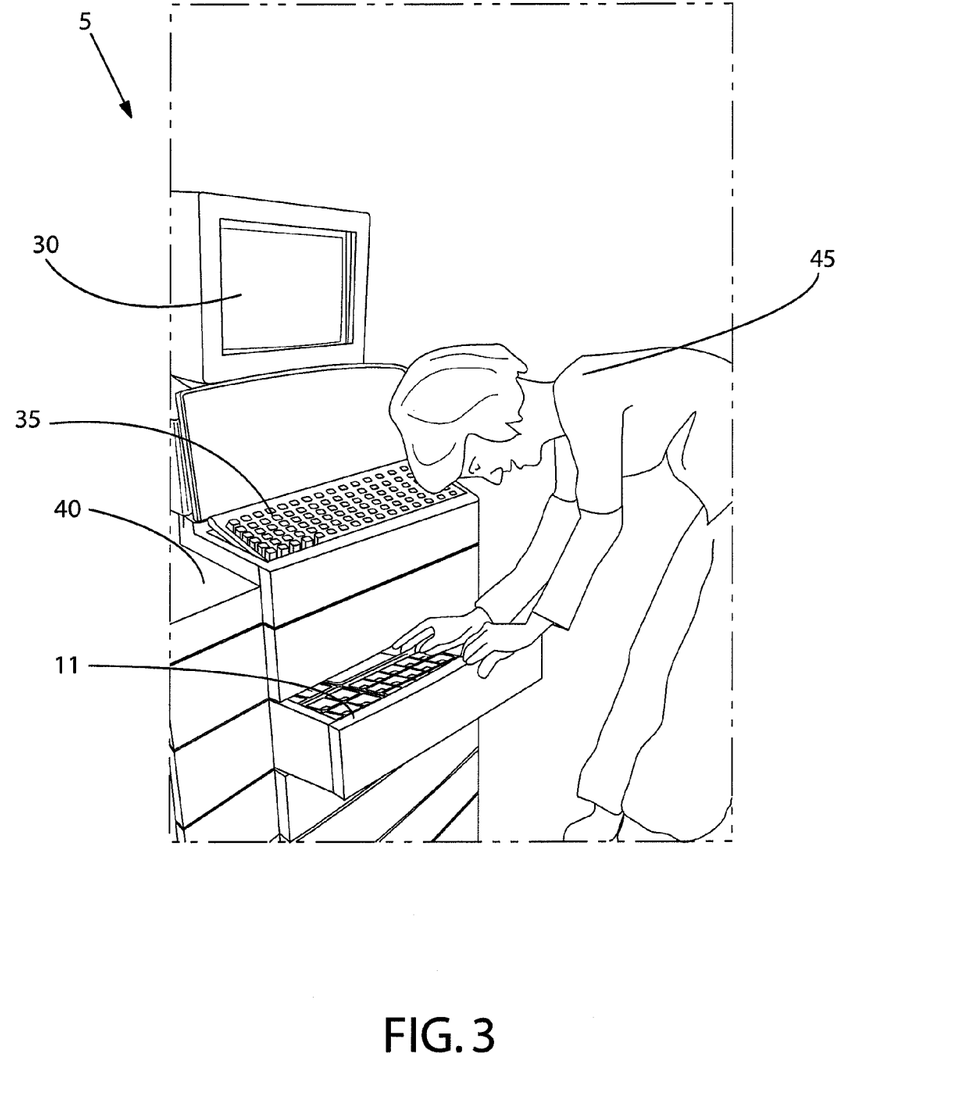
FIG. 3 illustrates a user accessing a drawer of the storage device in accordance with one exemplary embodiment of the present invention.

Once the user has initially interfaced with the cabinet-level display device 30 and the cabinet-level user input device(s) 35, for example, to view and select a particular patient's list of medications and select a first medication to dispense, the automated storage device 5 may provide the user with access to a particular drawer 10 in which the selected medication is stored. For example, a first identified drawer 11 may be unlocked, and the cabinet-level display device 30 may direct the user to access the unlocked drawer (e.g., by identifying the drawer with a number or other designation). In some cases, the first identified drawer 11 may both be unlocked and partially opened by the storage device 5 as an indication to the user of which drawer is to be accessed, as shown in FIG. 3.

In some cases, the cabinet-level display device 30 may also direct the user 45 as to which pocket 15 should be accessed to dispense the selected medication. A conventional storage device may, for example, indicate the particular pocket via an LED or other indicator located on the particular pocket to be accessed. In this way, the user would, upon looking into the identified drawer, visually determine which pocket is to be accessed. Upon dispensing medication from the indicated pocket, however, the user would have to change position (e.g., from leaning over to access the drawer to standing up) to interface with the cabinet-level display device 30 and/or the cabinet-level user input device 35 to enter inventory information for the accessed pocket and/or select another medication to dispense. In cases where multiple storage devices use a single cabinet-level display device 30 and/or a single cabinet-level user input device 35, the user may even have to take a few steps from the particular storage device being accessed to the location of the cabinet-level display device or user input device. Constant reference to a single cabinet-level display device 30 and/or the cabinet-level user input device 35 may lead to additional time spent by the user in interfacing with the storage device and less time with patients.

Figure 4:
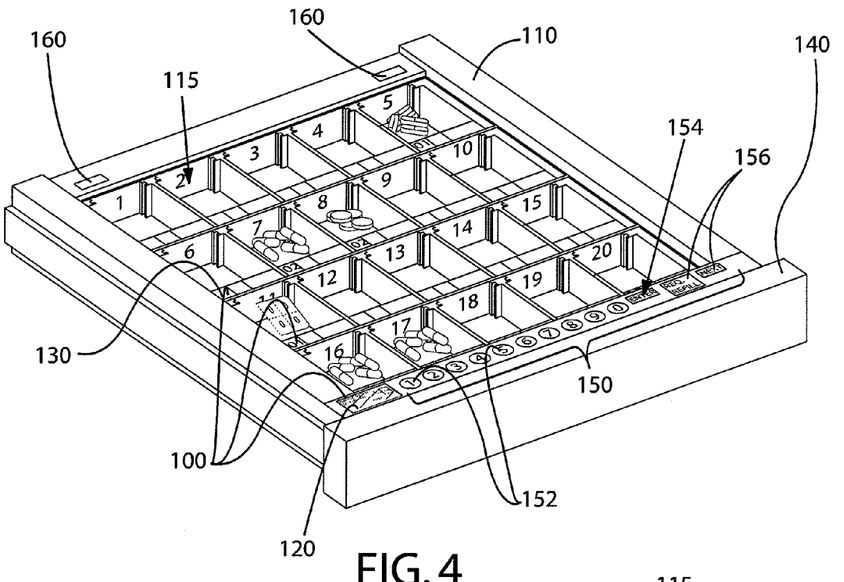
FIG. 4 is a perspective view of a drawer of a storage device in accordance with one exemplary embodiment of the present invention.

Accordingly, embodiments of the storage device, method, and computer program product include a plurality of drawer-level display devices 100, shown in FIG. 4. Each drawer-level display device 100 may be associated with and disposed on a particular drawer 110. Each drawer-level display device 100 may be configured to present a user with medication information (described above) for a selected medication stored in the associated drawer 110. In particular, the medication information may include at least one of a name of the selected medication (e.g., the chemical name of the medication, a common name for the medication used in the industry, a chemical compositions for the medication, and/or a code or alpha-numeric designation identifying the medication, such as a system designator for the particular medication), a quantity of the selected medication to be dispensed, a dosage of the medication to be dispensed, and/or medication inventory information. In this way, a user can have direct access to information required for completing a dispensing operation at the identified (accessed) drawer and does not need to refer back to the cabinet-level display device 30 (for example, if the nurse had forgotten how many units were to be dispensed according to the prescription). In other words, the information needed to complete a dispensing operation that is in progress can be found at the drawer-level, where the user's attention is already focused.

The drawer-level display devices 100 may be main drawer-level display devices 120, secondary drawer-level display devices 130, or may include both main drawer-level display devices and secondary drawer-level display devices. For example, at least some of the drawer-level display devices 100 may be main drawer-level display devices 120. Each main drawer-level display device may be disposed proximate a leading edge 140 of the respective associated drawer 110, such that upon opening the drawer, the user would quickly see the main drawer-level display device, even if the drawer is not fully open. In other cases, however, the main drawer-level display device 120 may be located elsewhere on the drawer 110, such as on a front panel or on the side of each drawer and may be visible to the user even when the drawer is closed.

Figure 4A:
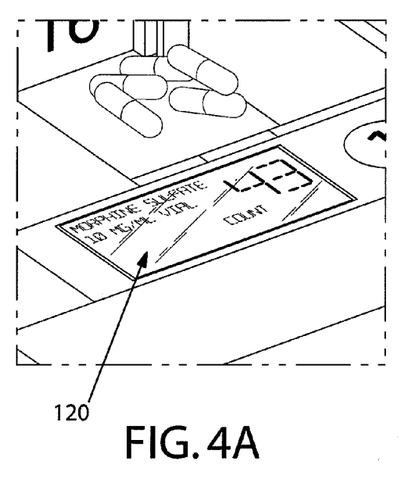
FIG. 4A illustrates a detail view of a main drawer-level display device of the storage device of FIG. 4 according to an exemplary embodiment of the present invention.

Each drawer 110 may have one main drawer-level display device 120 associated with it, and thus the user may be able to view at least certain medication information relating to the medication in the particular associated drawer via the main drawer-level display device. For example, as shown in FIG. 4A, the main drawer-level display device 120 may be configured to present to the user a name of the selected medication to be dispensed, a quantity of the medication to be dispensed, a prescribed dosage, a location of the selected medication (e.g., pocket identifier), and/or an inventory of the selected medication that is stored in the identified pocket, among other things. The main drawer-level display device 120 may be an LCD (liquid crystal display) screen, for example. Moreover, the information displayed via the main drawer-level display device 120 may be configurable by the user, such that only certain information is displayed.

Figure 4B:
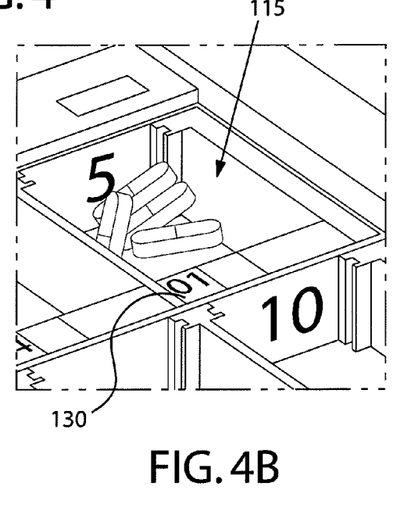
FIG. 4B illustrates a detail view of a secondary drawer-level display device of the storage device of FIG. 4 according to an exemplary embodiment of the present invention.

In other cases, at least some of the drawer-level display devices may be secondary drawer-level display devices 130, and each secondary drawer-level display device may be associated with and disposed proximate at least one of the pockets 115 defined by the associated drawer 110. For example, each pocket 115 may have a dedicated secondary drawer-level display device 130 associated with it, as shown in FIG. 4B. In other cases, however, two or more pockets may share the same secondary drawer-level display device. Each secondary drawer-level display device 130 may be configured to present to a user a quantity of the selected medication to be dispensed from the associated pocket. For example, in FIG. 4B, the selected medication is stored in Pocket 5. Accordingly, the secondary drawer-level display device 130 associated with Pocket 5 is activated and indicates that 2 units of the selected medication are to be dispensed. In other words, the display of the number "2" on the secondary drawer-level display device 130 in this case serves dual purposes—it both identifies which pocket is the identified pocket from which the selected medication is to be dispensed, and it indicates the quantity of the selected medication to be dispensed from that pocket. In this regard, the secondary drawer-level display device 130 may include one or more of an LCD, LED (light emitting diode), or other similar display technology.

Thus, in some embodiments, each drawer 110 includes both a main drawer-level display device 120 and a number of secondary drawer-level display devices 130 (e.g., one for each pocket 115) configured as described above. In addition, the storage device 5 may in some cases include a number of drawer-level user input devices 150, each of which is associated with and disposed on a particular compartment 110, for example, on each drawer as shown in FIG. 4. Each drawer-level user input device 150 may be configured to receive input from a user regarding an inventory of the selected medication stored in an identified pocket defined by the associated drawer (e.g., the pocket in which the selected medication is stored).

For example, as depicted in FIG. 4, the drawer-level user input device 150 may include a series of numerical buttons 152, e.g., 1 through 9, which a user may selectively depress to enter a count of the medication remaining in the identified pocket after the selected medication was dispensed. Other buttons may also be provided to facilitate entry of inventory or other information, such as an "Enter" button 154. The buttons may be dedicated "hard" buttons, or, in some cases, "soft" or smart buttons may be provided, such as through labels for a single physical button that are provided on an LCD to allow button functions to be dynamically changed.

In addition, certain key workflow function buttons 156 may be provided to allow the drawer-level user input device to receive input from the user selecting a workflow function. For example, more commonly selected workflow functions, such as "Request Refill" and "Next" may be represented to allow the user to perform workflow functions without referring back to the cabinet-level user input device 35. The "Request Refill" button may, for example, be depressed when the user has dispensed the last medication from a particular pocket, and the pocket would need to be refilled. Similarly, the "Next" button may be depressed by the user to indicate that one dispensing operation is complete and that the user is ready to be directed to the next medication to be dispensed. Additional workflow function buttons may include "Skip," "Cancel," "Yes," and "No," among others.

Although the drawer-level user input device 150 is shown in FIG. 4 as being located near the leading edge 140 of the drawer 110, near the main drawer-level display device 120, all or parts of the drawer-level user input device (e.g., one or more of the buttons) may be located elsewhere on the drawer, such as on the front of the drawer, on one or both sides, or dispersed at different locations on the drawer. For example, one or more workflow function buttons (e.g., the "Next" button) 156 may be located at each pocket, such as near each secondary drawer-level display device 130.

Figure 5:
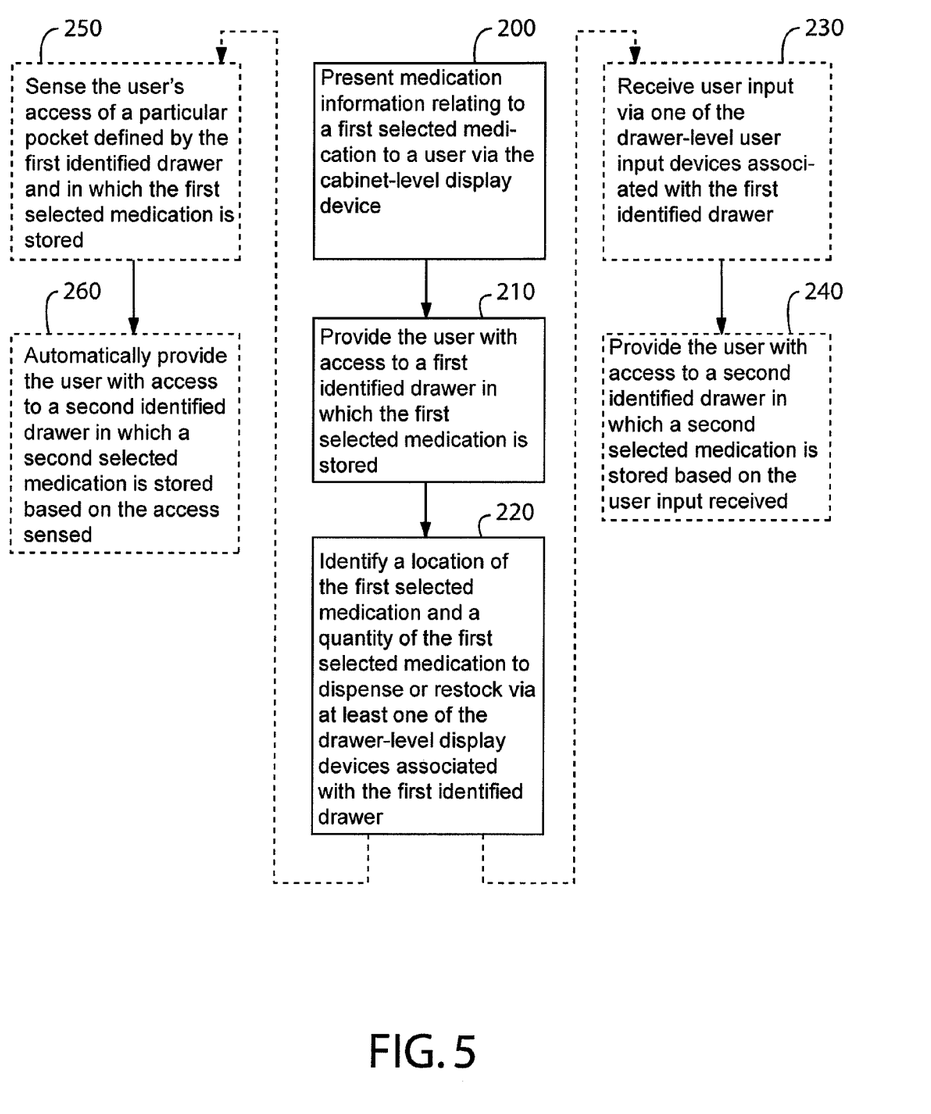
FIG. 5 is a flow chart illustrating a method of dispensing medication from a storage device according to an exemplary embodiment of the present invention.
Figure 6:
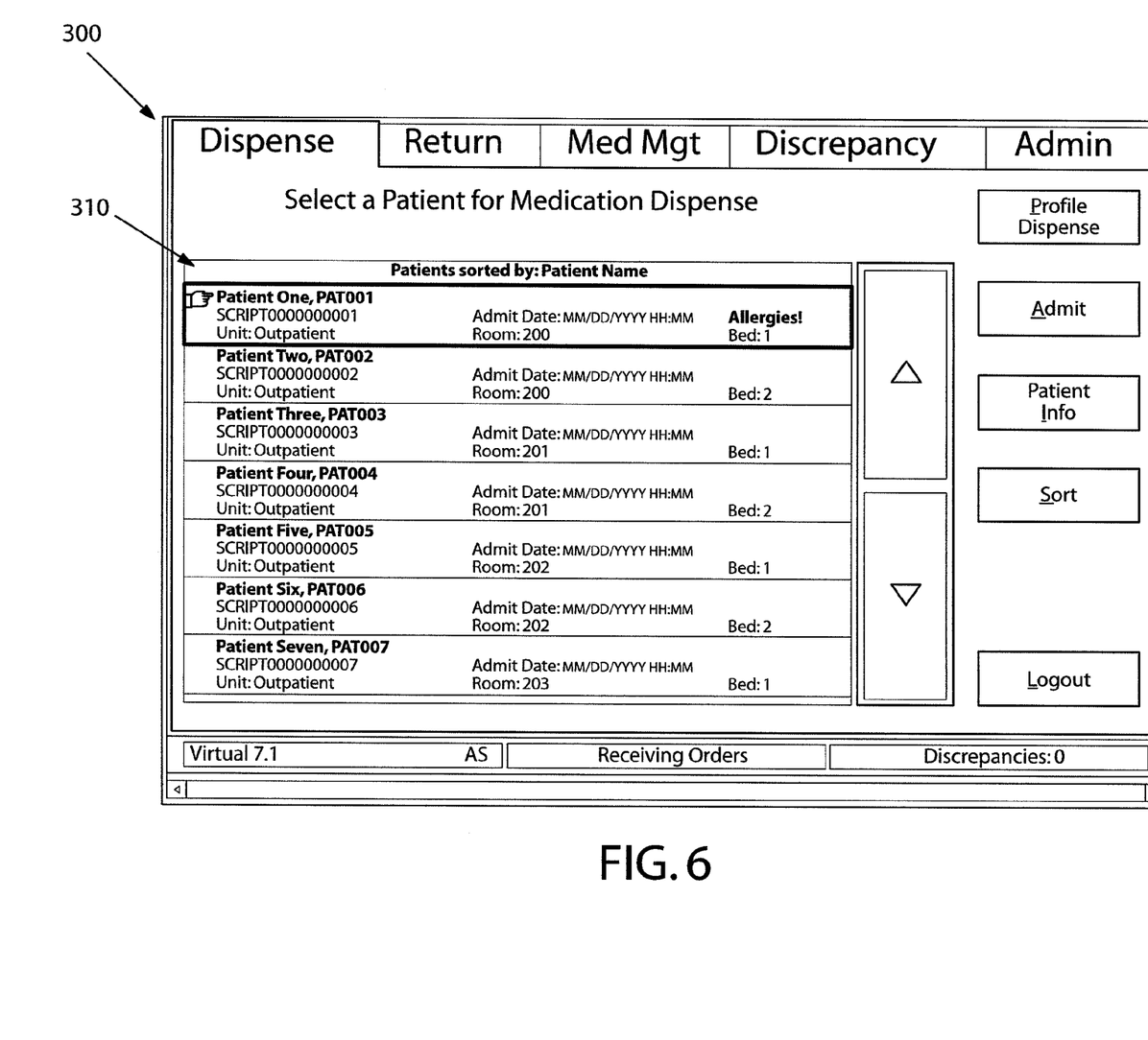
FIG. 6 shows an example of a screen displayed to a user for selecting a patient to whom medication will be dispensed according to an exemplary embodiment of the present invention.
Figure 7:
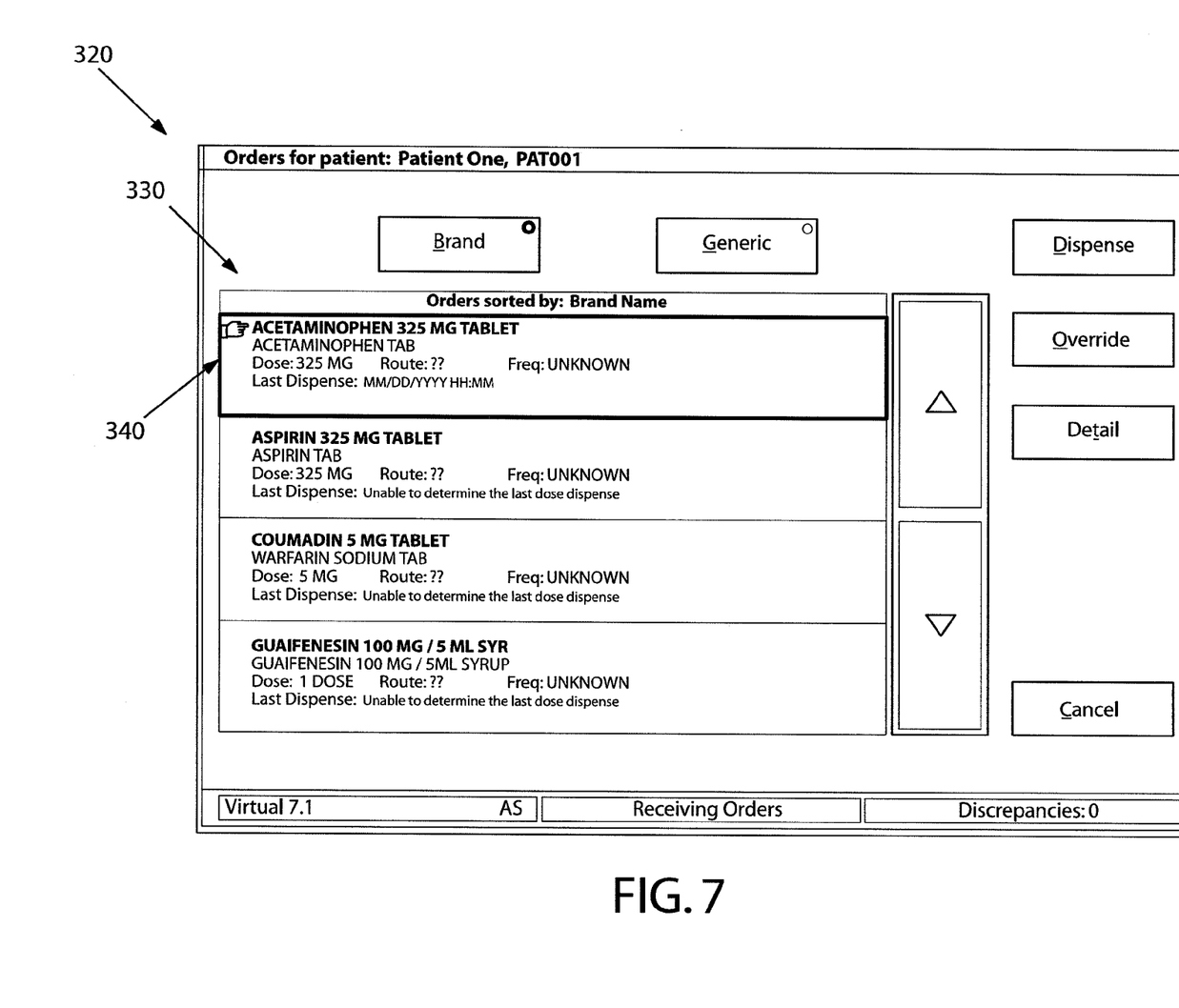
FIG. 7 shows an example of a screen displayed to a user for selecting a first medication to dispense according to an exemplary embodiment of the present invention.

With reference to the method flowchart provided in FIG. 5, for example, medication information relating to a first selected medication may initially be presented to a user via the cabinet-level display device 30. Block 200. For example, upon providing identification credentials showing that a user has access to medication stored in the storage device, the user may be presented with a screen 300 (FIG. 6) displayed on the cabinet-level display device 30 via interaction with the cabinet-level user input device 35. The screen 300 may provide the user with a list of patients 310 under the user's care, and the user may select one of the patients using the cabinet-level user input device 35 to fill that particular patient's prescriptions. Selection of a particular patient's entry may bring the user to another screen 320 (FIG. 7) that lists the prescriptions, or orders 330, that are in the system for the selected patient. At this point, the user may select a first selected medication 340 to dispense (which, in the depicted example of FIG. 7 is "Acetaminophen 325 mg tablet"), and the system may in turn provide the user with access to a first identified drawer in which the first selected medication is stored. FIG. 5, Block 210. As noted above, the first identified drawer may be unlocked and/or opened to provide the user with access.

In some cases, the system may receive all of a user's requests for medications to dispense, and the system may then select the first selected medication to which the user should be directed based on the medication's location in the storage device. In other words, the system may determine the first selected medication based on workflow efficiency, rather than the particular order in which the user made his/her request.

Regardless, the system may identify a location of the first selected medication and a quantity of the first selected medication to dispense via at least one of the drawer-level display devices associated with the first identified drawer. Block 220. For example, a secondary drawer-level display device located at the pocket in which the first selected medication is stored may display the required quantity to be dispensed, thereby also indicating which pocket is to be accessed, as described above.

In cases in which the storage device also includes a number of drawer-level user input devices, as described above, user input may be received via a drawer-level user input device associated with the first identified drawer. FIG. 5, Block 230. For example, the user may enter a count of the medication remaining in the first identified drawer once the medication has been dispensed (e.g., inventory information) by depressing the number buttons 152 of the drawer-level user input device 150 (FIG. 4).

The user may be allowed access to a second identified drawer in which a second selected medication is stored based on the user input received. Block 240. For example, as described above with reference to FIG. 4, once the user has dispensed the first identified medication from the identified pocket 115, the user may depress the "Next" workflow function button 156 to prompt the system to proceed to the next medication to be dispensed. As a result, another pocket 115 may be identified in the same drawer 110 and a quantity of a second selected medication to be dispensed from the second identified pocket may be displayed to the user via the respective secondary drawer-level display device 130. If the second identified medication is stored in another drawer, the user may be prompted to close the open drawer, such as via a message displayed on the respective main drawer-level display device 120, or the open drawer may automatically be moved to a closed and locked position by the system and the second identified drawer may be unlocked/opened in its place.

In some embodiments, the storage device may include one or more sensors configured to detect pocket access by a user during a medication dispensing operation. For example, sensors 160 may be provided on the drawer 110 that can sense when the user's hand has retrieved a medication from a particular pocket and can further sense which pocket was accessed. The sensors 160 may be in the form of light sensors (e.g., optical sensors) and may be provided on the drawer to cover all the pockets defined by the drawer or on each individual pocket. For example, in cases where a pocket has a single unit dose stored therein, an optical sensor may be disposed on the pocket to detect when the pocket is empty.

Alternatively or in addition, the sensors 160 may be in the form of a weight sensor, which can detect when medication has been removed from a particular pocket 115 based on the change of weight of the pocket contents. In still other embodiments, for example, where a pocket 115 is configured to have a lid, the lid may have a sensor that is configured to detect when the lid is open and when the lid is closed and/or locked. The sensor may, in this case, be located on a hinge of the lid.

Thus, in some cases, the user's access of a particular pocket defined by the first identified drawer and in which the first selected medication is stored may be sensed. FIG. 5, Block 250. The user may then be automatically provided with access to a second identified drawer in which a second selected medication is stored based on the access sensed. Block 260.

Stated differently, in situations where the user needs to fill a prescription for multiple medications, the user need only reference one or both of the main drawer-level display device 120 and the secondary drawer-level display devices 130 (FIG. 4) to move from one medication to the next, as opposed to continually switching between a standing up position (FIG. 2) and a stooped or crouched position (FIG. 3) (and potentially also walking a few steps) to view the cabinet-level display device 30 and/or interact with the cabinet-level user input device 35 located at the accessed storage device or a separate, nearby storage device, as described above. In addition, embodiments of the storage device, system, and method described above allow the workflow process associated with dispensing medication to change from the typical system-driven workflow process to a user-driven workflow process.

In this regard, in some cases, the secondary drawer-level display devices 130 may each be configured to sequentially identify a single pocket 115 defined by the associated drawer from which the selected medication is to be dispensed. In other words, as described above with reference to FIG. 5, only one secondary drawer-level display device at a time within a particular drawer may indicate the identified pocket and provide a quantity to be dispensed. Once one medication dispensing operation has been completed (e.g., as indicated by the user through the depressing of a "Next" button or detected by sensors), the next medication is made available for dispensing by the system, such as by illuminating the next secondary drawer-level display device (e.g., in the same drawer) to provide a quantity of that medication to be dispensed. Thus, the user is governing the speed and progress of the dispensing workflow, rather than the system continually prompting the user to take the next action in the workflow.

Alternatively, the system may be configured to identify substantially simultaneously (e.g., via secondary drawer-level display devices) more than one pocket defined by the associated drawer from which the selected medication is to be dispensed. Referring to FIG. 4, for example, under this scenario, the secondary drawer-level display devices 130 associated with Pockets 5, 7, 8, and 9 may, at the same time, display the quantities of the respective medications to be dispensed, giving the user the choice of which of the four medications to dispense first. Again, the user is governing the speed and progress of the dispensing workflow and is prompting the system to proceed when the user is ready for the next action, rather than vice versa. In this way, the workflow can be streamlined and customized for each particular user, resulting in less time and effort of the user at the storage device.

Figure 8:
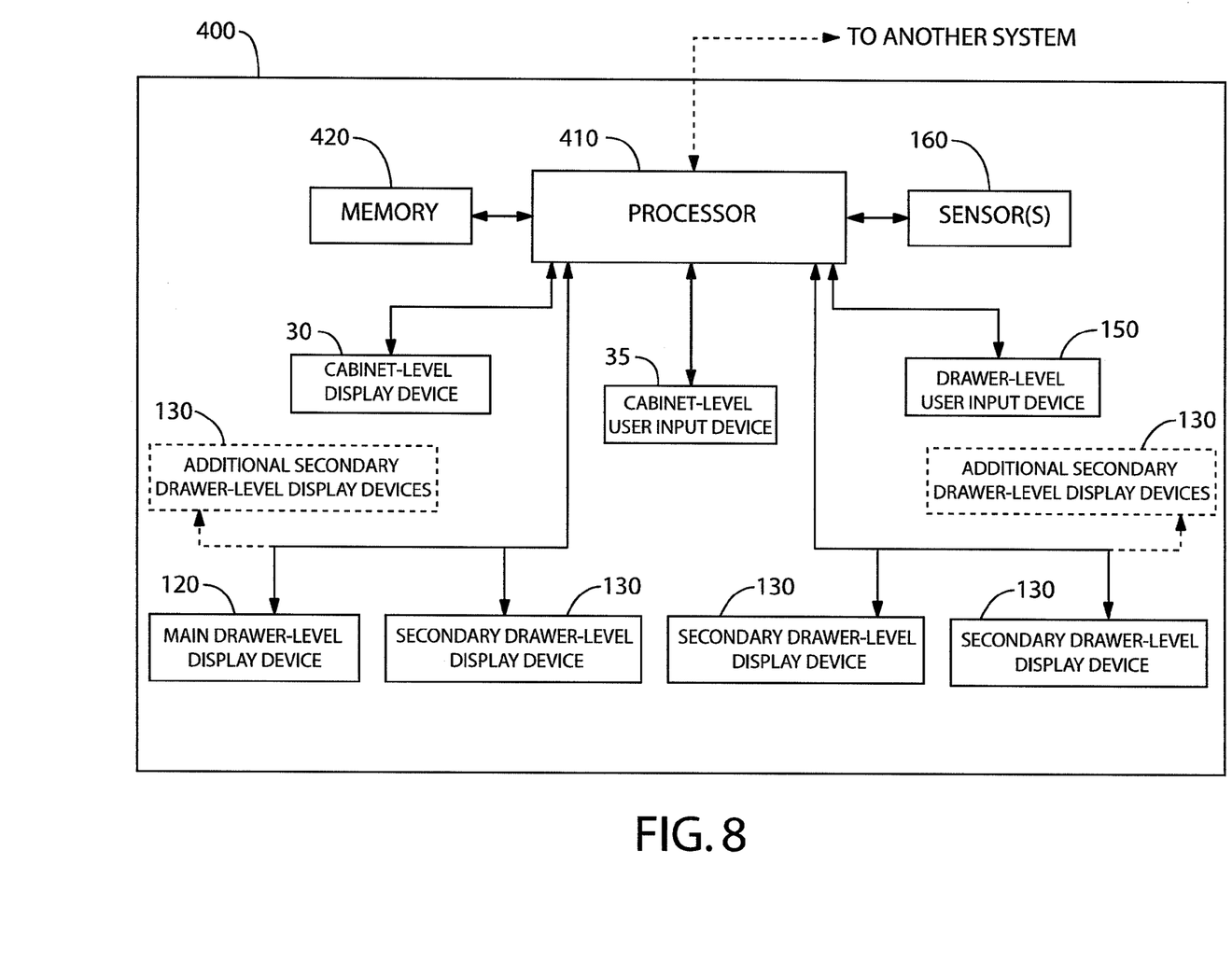
FIG. 8 is a schematic representation of a system for dispensing medication from a storage device according to an exemplary embodiment of the present invention.

With the above description in mind, and with reference to FIG. 8, in some embodiments, a system 400 is provided for dispensing medication from a storage device. The system 400 may include a processor 410 configured to access medication information, a cabinet-level display device 30 in communication with the processor and configured to present to a user at least one item of information from the accessed medication information, and a plurality of secondary drawer-level display devices 130 in communication with the processor. As noted above, each secondary drawer-level display device 130 may be associated with at least one of a plurality of pockets 115 defined by a particular drawer 110, and each may be configured to identify at least one of the associated pockets from which a selected medication is to be dispensed and to present to the user a quantity of the selected medication to be dispensed from the associated pocket. In some cases, the system 400 may further include a cabinet-level user input device 35, as described above.

As described above, in some cases, a plurality of main drawer-level display devices 120 that are in communication with the processor 410 are also provided. Each main drawer-level display device 120 may be associated with one of a plurality of drawers of the cabinet, and each main drawer-level display device may be configured to present to the user a name of the selected medication that is to be dispensed from the associated drawer. The name of the selected medication may include the chemical name of the medication, a common name for the medication used in the industry, a chemical compositions for the medication, and/or a code or alpha-numeric designation identifying the medication, such as a system designator for the particular medication. Each main drawer-level display device 120 may be disposed proximate a leading edge of the respective associated drawer or elsewhere, such as on a front or a side of the associated drawer. Similarly, each secondary drawer-level display device 130 may only be accessible to the user when the associated drawer is accessed by the user. In other words, when the drawer is closed and/or locked, in some cases the user would not be able to access either the main drawer-level display device or the secondary drawer-level display devices, depending on where the devices were located.

Similarly, the system 400 may include a plurality of drawer-level user input devices 150 in communication with the processor 410, and each drawer-level user input device may be associated with a particular drawer and may be configured to receive input from the user regarding an inventory of the selected medication stored in the identified pocket of the associated drawer 110, as described above. The drawer-level user input device 150 may be located proximate the main drawer-level display device 120 and/or the secondary drawer-level display devices 130 and may also be accessible to the user only when the associated drawer is accessed by the user, depending on its location. As noted above, one or more sensors 160 may also be included as part of the system 400, and the sensors may be configured to detect pocket access by the user during a medication dispensing operation. The processor, in turn, may be configured to present medication information regarding an additional selected medication to be dispensed based on feedback received from the sensor(s) 160.

As noted above, the system 400 may be disposed at a particular storage device (e.g., on a particular floor or in a particular unit of a hospital); however, one or more of the systems for different storage devices may be in communication with each other. Thus, different systems may communicate inventory needs between each other, compare trends and user access, and perform other functions through communications with each other and/or other systems of the healthcare facility.

Exemplary embodiments of the present invention have been described above with reference to block diagrams and flowchart illustrations of methods, apparatuses (e.g., systems) and computer program products. It will be understood that each operation, action, step and/or other types of functions shown in the diagram (FIG. 5), and/or combinations of functions in the diagram, can be implemented by various means. Dashed lines in FIG. 5 indicate optional steps of the method. Means for implementing the functions of the flow diagram, combinations of the actions in the diagrams, and/or other functionality of example embodiments of the present invention described herein, may include hardware and/or a computer program product including a computer-readable storage medium (as opposed to or in addition to a computer-readable transmission medium) having one or more computer program code instructions, program instructions, or executable computer-readable program code instructions stored therein.

For example, program code instructions associated with FIG. 5 may be stored on one or more storage devices, such as a memory 420, and executed by one or more processors, such as processor 410, shown in FIG. 8. Additionally or alternatively, one or more of the program code instructions discussed herein may be stored and/or performed by distributed components, such as those discussed in connection with system 400. As will be appreciated, any such program code instructions may be loaded onto computers, processors, other programmable apparatuses or network thereof from one or more computer-readable storage mediums to produce a particular machine, such that the particular machine becomes a means for implementing the functions of the actions discussed in connection with, e.g., FIG. 5 and/or the other drawings discussed herein. As such, FIG. 5 showing data flows may likewise represent program code instructions that may be loaded onto a computer, processor, other programmable apparatus or network thereof to produce a particular machine.

The program code instructions stored on the programmable apparatus may also be stored in a nontransitory computer-readable storage medium that can direct a computer, a processor (such as processor 410) and/or other programmable apparatus to function in a particular manner to thereby generate a particular article of manufacture. The article of manufacture becomes a means for implementing the functions of the actions discussed in connection with, e.g., FIG. 5. The program code instructions may be retrieved from a computer-readable storage medium and loaded into a computer, processor, or other programmable apparatus to configure the computer, processor, or other programmable apparatus to execute actions to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel by one or more machines, such that multiple instructions are retrieved, loaded, and/or executed together. Execution of the program code instructions may produce a computer-implemented process such that the instructions executed by the computer, processor, other programmable apparatus, or network thereof provides actions for implementing the functions specified in the actions discussed in connection with, e.g., the process illustrated in FIG. 5.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A storage device for dispensing medication comprising:
at least one drawer, wherein each drawer defines a plurality of pockets and each pocket is configured to store at least one medication; and
a plurality of drawer-level display devices, wherein each of the drawer-level display devices is associated with and disposed on a particular drawer, the plurality of drawer-level display devices, for each associated drawer, comprising a main drawer-level display device disposed on the associated drawer and a plurality of secondary drawer-level display devices, wherein each secondary drawer-level display device is associated with and disposed proximate at least one of the pockets defined by the associated drawer,
wherein the main drawer-level display device is configured to present a user with a name of the selected medication to be dispensed or restocked and an inventory of the selected medication stored in an identified pocket defined by the associated drawer, and
wherein the secondary drawer-level display devices are each configured to present to a user a quantity of the selected medication to be dispensed from or restocked to the associated pocket.

2. The storage device of claim 1, wherein the at least one drawer is slideably received within the storage device.

3. The storage device of claim 1, wherein the drawer-level user input device is configured to receive input from a user selecting a workflow function.

4. The storage device of claim 1 further comprising a sensor configured to detect pocket access by a user during a medication dispensing or restocking operation.

5. The storage device of claim 1, wherein the secondary drawer-level display devices are each configured to sequentially identify a single pocket defined by the associated drawer from which the selected medication is to be dispensed or to which the selected medication is to be restocked.

6. The storage device of claim 1, wherein the secondary drawer-level display devices are collectively configured to identify substantially simultaneously more than one pocket defined by the associated drawer from which the selected medication is to be dispensed or to which the selected medication is to be restocked.

7. The storage device of claim 1 further comprising a cabinet-level display device associated with the one or more drawers of the storage device and configured to present medication information related to any of the associated drawers.

8. The storage device of claim 1 further comprising a cabinet-level user input device associated with the one or more drawers of the storage device and configured to receive input from a user related to any of the associated drawers.

9. A system for dispensing medication from a storage device, wherein the storage device comprises a plurality of drawers, the system comprising:
a processor configured to access medication information;

a plurality of main drawer-level display devices in communication with the processor, wherein each main drawer-level display device is associated with a drawer of the storage device; and a plurality of secondary drawer-level display devices in communication with the processor, wherein each main drawer-level display device is configured to present to the user a name of a selected medication that is to be dispensed from or restocked to the associated drawer and an inventory of the selected medication stored in an identified pocket defined by the associated drawer, and wherein each secondary drawer-level display device is associated with and disposed proximate at least one of a plurality of pockets defined by a particular drawer, and wherein each secondary drawer-level display device is configured to identify at least one of the associated pockets from which the selected medication is to be dispensed and to present to a user a quantity of the selected medication to be dispensed from the identified pocket.

10. The system of claim 9, wherein each secondary drawer-level display device is configured to identify at least one of the associated pockets to which the selected medication is to be restocked.

11. The system of claim 9, wherein each secondary drawer-level display device is only accessible to the user when the associated drawer is accessed by the user.

12. The system of claim 9, wherein each main drawer-level display device is disposed proximate a leading edge of the respective associated drawer and is accessible to the user when the associated drawer is accessed by the user.

13. The system of claim 9 further comprising a plurality of drawer-level user input devices in communication with the processor, wherein each drawer-level user input device is associated with a particular drawer and is configured to receive input from the user regarding an inventory of the selected medication stored in the identified pocket of the associated drawer.

14. The system of claim 13, wherein each drawer-level user input device is configured to receive input from the user regarding a workflow function.

15. The system of claim 9 further comprising a sensor in communication with the processor, wherein the sensor is configured to detect pocket access by the user during a medication dispensing or restocking operation, and wherein the processor is configured to present medication information regarding an additional selected medication to be dispensed or restocked based on feedback received from the sensor.

16. The system of claim 9 further comprising a cabinet-level display device in communication with the processor and configured to present to the user at least one item of information from the accessed medication information.

17. A method of dispensing medication from a storage device comprising:

presenting medication information relating to a first selected medication to a user via a cabinet-level display device associated with a storage device comprising at least one drawer, wherein each drawer defines a plurality of pockets and each pocket is configured to store at least one medication;

providing the user with access to a first identified drawer in which the first selected medication is stored; and identifying a location of the first selected medication and a quantity of the first selected medication to dispense via at least one of a plurality of drawer-level display devices associated with and disposed on the first identified drawer, wherein each of the drawer-level display devices is associated with and disposed on a particular drawer, the plurality of drawer-level display devices, for each associated drawer, comprising a main drawer-level display device disposed on the associated drawer and a plurality of secondary drawer-level display devices, wherein each secondary drawer-level display device is associated with and disposed proximate at least one of the pockets defined by the associated drawer, wherein the main drawer-level display device is configured to present a user with a name of the selected medication to be dispensed or restocked and an inventory of the selected medication stored in an identified pocket defined by the associated drawer, and wherein the secondary drawer-level display devices are each configured to present to a user a quantity of the selected medication to be dispensed from or restocked to the associated pocket.

18. The method of claim 17, wherein the step of identifying the location and the quantity of the first selected medication comprises identifying a location of the first selected medication and a quantity of the first selected medication to restock via at least one of the plurality of drawer-level display devices.

19. The method of claim 17, wherein the storage device further comprises a plurality of drawer-level user input devices, wherein at least one of the drawer-level user input devices is associated with a particular drawer and is disposed on the associated drawer, the method further comprising the step of receiving user input via a drawer-level user input device associated with the first identified drawer.

20. The method of claim 19 further comprising the step of providing the user with access to a second identified drawer in which a second selected medication is stored based on the user input received.

21. The method of claim 17 further comprising the steps of:

sensing the user's access of a particular pocket defined by the first identified drawer and in which the first selected medication is stored; and automatically providing the user with access to a second identified drawer in which a second selected medication is stored based on the access sensed.

22. A computer program product comprising at least one computer-readable storage medium having computer-readable program code portions stored therein, the computer-readable program code portions comprising:

a first executable portion configured for presenting medication information including a first selected medication to a user via a cabinet-level display device;

a second executable portion configured for allowing the user access to a first identified drawer in which the first selected medication is stored;

a third executable portion configured for presenting a user with a name of the selected medication to be dispensed or restocked and an inventory of the selected medication stored in an identified pocket defined by the first identified drawer via a main drawer-level display device associated with and disposed on the first identified drawer; and a fourth executable portion configured for identifying a location of the first selected medication and a quantity of the first selected medication to dispense via at least one secondary drawer-level display device, wherein each secondary drawer-level display device is associated with and disposed proximate the identified pocket.

23. The computer program product of claim 22 further comprising a fifth executable portion configured for receiving user input at a drawer-level user input device regarding a dispensing or restocking operation, wherein the drawer-level user input device is associated with a particular drawer and is disposed on the associated drawer.

24. The computer program product of claim 23 further comprising a sixth executable portion configured for allowing the user access to a second identified drawer in which a second selected medication is stored based on the user input received via a drawer-level user input device associated with the first identified drawer.

25. The computer program product of claim 22 further comprising:
- a fifth executable portion configured for sensing the user's access of a particular pocket defined by the first identified drawer and in which the first selected medication is stored; and
- a sixth executable portion configured for automatically allowing the user access to a second identified drawer in which a second selected medication is stored based on the access sensed without requiring user interaction with the cabinet-level display device between dispensing or restocking operations related to the first and second selected medications.

* * * * *